United States Patent [19]

Irino et al.

[11] Patent Number: 5,527,689
[45] Date of Patent: Jun. 18, 1996

[54] ENZYMATIC COUPLING OF L-PHENYLALANINE METHYL ESTER AND N-BENZYLOXYCARBONYL-ASPARTIC ACID

[75] Inventors: Shigeaki Irino; Shin-ichiro Nakamura, both of Yamaguchi; Kiyotaka Oyama, Tokyo-prefecture, all of Japan; Peter J. L. M. Quaedflieg, Geleen; Theodorus J. G. M. Van Dooren, Roermond, both of Netherlands

[73] Assignee: Holland Sweetener Company V.o.F., Maastricht, Netherlands

[21] Appl. No.: 366,592

[22] Filed: Dec. 29, 1994

[30] Foreign Application Priority Data

Jan. 20, 1994 [NL] Netherlands ............................ 9400092

[51] Int. Cl.$^6$ .............................. C12P 21/02; C12N 9/50; C12N 9/52; C12N 9/54
[52] U.S. Cl. ...................... 435/68.1; 435/219; 435/220; 435/221; 435/222; 560/38; 560/41; 560/49
[58] Field of Search .................................. 435/68.1, 219, 435/220, 221, 222; 560/38, 41, 49

[56] References Cited

U.S. PATENT DOCUMENTS

| | | |
|---|---|---|
| 4,116,768 | 9/1978 | Isowa et al. . |
| 4,119,493 | 10/1978 | Isowa et al. . |
| 4,256,836 | 3/1981 | Isowa et al. . |
| 4,436,925 | 3/1984 | Isowa et al. . |
| 4,487,717 | 12/1984 | Okama et al. ............................ 424/177 |
| 4,710,583 | 12/1987 | Chmurny et al. ....................... 435/68.1 |
| 5,302,743 | 4/1994 | Katoh et al. ............................... 560/49 |

FOREIGN PATENT DOCUMENTS

| | | |
|---|---|---|
| 0149594 | 7/1985 | European Pat. Off. . |
| 2201855 | 11/1986 | European Pat. Off. . |
| 2378747 | 8/1978 | France . |
| 2589490 | 5/1987 | Germany . |
| 2250023 | 5/1992 | United Kingdom . |

OTHER PUBLICATIONS

Chemical Abstracts, vol. 120, No. 35, Abstract No. 48817v 31 Jan. 1994.

Journal of the Chemical Society, Perkin Transactions II, 356–360 (1981).

*Primary Examiner*—Herbert J. Lilling
*Attorney, Agent, or Firm*—Cushman Darby & Cushman

[57] ABSTRACT

The invention relates to a process for the preparation of N-benzyloxycarbonyl-α-L-aspartyl-L-phenylalanine methyl ester by enzymatic coupling of N-benzyloxycarbonyl-L-aspartic acid and L-phenylalanine methyl ester in an aqueous medium with formation of a precipitate, the coupling reaction being effected with (virtually) equimolar quantities of N-benzyloxycarbonyl-L-aspartic acid and L-phenylalanine methyl ester under the influence of a neutral protease at an initial pH of from 4.5 to 6.0 and in the presence of from 3 to 25%, calculated as per cent by weight based on the total reaction mixture, of an alkali metal salt, alkaline earth metal salt or ammonium salt.

20 Claims, No Drawings

ENZYMATIC COUPLING OF L-PHENYLALANINE METHYL ESTER AND N-BENZYLOXYCARBONYL-ASPARTIC ACID

FIELD OF THE INVENTION

The invention relates to a process for the preparation of N-benzyloxycarbonyl-α-L-aspartyl-L-phenylalanine methyl ester by high-conversion enzymatic coupling of N-benzyloxycarbonyl-L-aspartic acid and L-phenylalanine methyl ester in an aqueous medium with formation of a precipitate.

BACKGROUND OF THE INVENTION

N-protected α-L-aspartyl-L-phenylalanine methyl ester, such as in particular N-benzyloxycarbonyl-α-L-aspartyl-L-phenylalanine methyl ester, is an important precursor of the "intense sweetener" aspartame, a product having a sweetening power of approximately 200 times that of sucrose and with an excellent taste profile without, for example, the bitter aftertaste of other intense sweeteners such as, for example, saccharin and cyclamate. The sweetener aspartame is used, inter alia, in a wide range of products such as soft drinks, sweets, "table-top sweeteners", pharmaceuticals, etc.

Various methods are known for the preparation of aspartame. In addition to chemical preparation methods there are also enzymatic preparation methods, which owe their importance primarily to the fact that enzymatic coupling takes place in a stereoselective and regioselective manner. Enzymatic L,L-coupling of N-protected aspartic acid, in particular of N-benzyloxycarbonyl-aspartic acid (hereinafter also designated by Z-Asp), and L- (or DL-) phenylalanine methyl ester, or of acid salts derived therefrom such as, for example, the hydrochloride salt (in the following also designated by PM), with formation of an N-protected aspartame precursor, has been thoroughly studied and described to date. An overview of aspartame preparation methods is given by K. Oyama in Chapter 11 (pp. 237–247) of "Chirality in Industry", John Wiley & Sons Ltd., 1992.

The enzymatic coupling reaction in question, which as a rule is carried out at a pH of from 6 to 7.5 in the presence of a neutral protease, in particular of a metallo-protease such as, for example, thermolysin, is an equilibrium-controlled reaction. In order to achieve high degrees of conversion in such enzymatic coupling reactions, specific measures are necessary according to the state of the art. Thus, for example, U.S. Pat. No. 4,165,311 (which is regarded to be the nearest state of the art) makes use of the fact that the equilibrium in the coupling reaction can be shifted to the right by the formation of a precipitating addition compound of N-protected aspartame, in particular of N-benzyloxycarbonyl-α-L-aspartyl-L-phenylalanine methyl ester (hereinafter also designated by Z-APM), with D- or L-phenylalanine methyl ester present in the reaction mixture. Such addition compounds of the aspartame precursor are also designated by Z-APM.D-PM or Z-APM.L-PM, respectively. In order to form such addition products it is desirable, according to the state of the art, for the coupling reaction of Z-Asp and L-PM to be carried out with at least double the molar quantity of L-PM with respect to Z-Asp, or in the presence of an at least equivalent amount of D-PM in order to achieve high degrees of conversion, i.e. >60%, preferably >80% based on Z-Asp. In practice, these enzymatic coupling reactions are therefore usually described in ratios of PM to Z-Asp of, for example, from 2.0 to 2.5:1 or higher. Although with such embodiments high degrees of conversion to the desired product are indeed achieved, these methods have a number of drawbacks, viz.:

(a) handling and further processing of the precipitate in order to obtain the ultimately desired aspartame (hereinafter: APM) is laborious, partly because the addition product is relatively difficult to filter and must be washed thoroughly in order to obtain APM which contains only small amounts of impurities;

(b) recovery and/or recirculation is necessary of the component(s) present in excess and of the non-APM component to be liberated from the precipitated addition product of the coupling product; if the coupling reaction is carried out with DL-PM, the remaining D-PM should, as a rule, when being processed, also be racemized, as a rule via DL-phenylalanine. These methods are therefore less suitable for application on a commercial scale.

It should be noted that WO-A-92/02617 describes an enzymatic coupling reaction of virtually equal amounts of Z-Asp and L-PM.HCl (in a molar ratio of approximately 1.2:1) in an aqueous medium and in the presence of acetic acid at pH=7. In this case, use is made of protease enzyme crystals immobilized by cross-linking, but the degree of conversion achieved is only approximately 20%. EP-A-0149594 describes the use of formyl-Asp (F-Asp) for an enzymatic coupling reaction in an aqueous medium in a 1:1 ratio of F-Asp to L-PM. However, because of the formation of the F-APM.L-PM addition product, the conversion of F-Asp remains distinctly below 50%, and the yield achieved in the process is found to be very low (approximately 12% after processing to give F-APM).

In the same way the article of Zhou F. et al. (in: Huaxue Fanying Goncheng Yu Gongyi, 1992, 8(4), pp 413–419 (in Chinese); abstract in Chemical Abstracts, 120 (no. 35), 31-1-94, abstract 48817v) describes amongst other things an experiment of 1:1 enzymatic coupling of Z-L-asp and L-PM at an initial pH of 6. However, also under these conditions, due to the usual formation of the ZAPM.PM addition product the conversion of Z-Asp is at best 46.1%. It should be noted that the L-PM conversion (of at most 92.2%) as reported by Zhou F. et al. accounts for the sum of the (chemical) coupling of L-PM into Z-APM and the concomittant precipitation of one equivalent of L-PM with Z-APM. There is no teaching in this article that chemical conversion of L-PM above 50% can be reached.

It should also be noted, incidentally, that the esters present in the coupling reaction system are relatively sensitive to chemical hydrolysis. Thus, PM is hydrolyzed to form phenylalanine (hereinafter also designated by Phe); Z-APM is hydrolyzed to form Z-protected aspartylphenylalanine (sometimes designated by Z-AP). This undesirable side reaction occurs especially at a pH >6, or >4, and is stronger the more the pH deviates from said values and the residence time under reaction conditions is longer.

Until now it has been generally assumed that in the enzymatic coupling of Z-Asp and L-PM, starting from equivalent or virtually equivalent amounts of Z-Asp and L-PM without the presence of a corresponding amount of D-PM, or without taking other measures to shift the coupling equilibrium, no conversions greater than 50%, calculated on the basis of Z-Asp, could be achieved. As far as the enzymatic coupling in an aqueous medium is concerned, Zhou and Huang (Indian J. Chem., 32B, pp 35–39, 1993) stated even recently that the optimum conditions for the reaction, using immobilized protease, are at a ratio of Z-Asp to PM of 1:4. It should be noted in this context that, when an immobilized protease is used (cf., e.g. Biotechnology, 3, pp. 459–464, 1985; Nakanishi et al.) much of the product formed is absorbed in the resin employed fox immobilization and has to be removed therefrom via a separate extraction step. The results achieved by Nakanishi et al. with a 1:1 ratio of Z-Asp to L-PM in an aqueous medium, a yield of at most 58% at a relatively low concentration (80 mM), are therefore irrelevant to industrial practice. Moreover, at such low concentrations, often used for determining initial reaction rates, coupling reaction proceeds without formation of a precipitate.

Alternative ways of shifting the coupling equilibrium have been described in, inter alia, (i) J. Org. Chem. 46, p. 5241 (1981): use of an immobilized protease and an organic solvent not miscible with water; similarly, JP-B-8533840, where yields of only approximately 20–30% are shown when use is made of 1:1 molar ratios; (ii) GB-A-2250023: use of immobilized protease and water-miscible organic solvent; similarly EP-A-0272564 in acetonitrile, where, while it is suggested that the ratio of N-protected Asp to L-PM can be between 10:1 and 1:10, the examples show, nevertheless, that only a considerable excess of L-PM is being considered and that in the case of stoichiometric or virtually stoichiometric ratios poor conversions and yields are obtained. Stoichiometric ratios are also called equimolar ratios. From the examples described in GB-A-2250023 it can likewise be seen, incidentally, that higher yields are achieved the higher the ratio of L-PM to N-protected Asp (at 2:1, the yield is approximately 85%, at 1:1 only approximately 50%). In such alternative embodiments, the shift of the equilibrium is not achieved by a precipitate being formed, but rather by the coupling product formed being transferred to the organic phase. Apart from cost-increasing aspects as a result of often unavoidable solvent losses when using organic solvents, another drawback of such alternative embodiments is that, during processing to produce aspartame, special measures must be taken to remove the organic solvents used in the coupling reaction. When adding (or carrying out the reaction in, or in the presence of, as the case may be) an organic solvent such as, for example, acetonitrile or dimethyl formamide, or substances such as di- and triglyme (see EP-A-0278190), as a rule only low yields of Z-APM and the like are achieved, unless the reaction is carried out at a high molar ratio of L-PM (.HCl) to Z-Asp.

It should additionally also be noted that it is not unusual, in the case of chemical coupling reactions (starting from N-protected aspartic anhydride, for example the N-formyl derivative, and L-Phe or L-PM), for the reaction to take place at stoichiometric or virtually stoichiometric ratios of the reactants, but this teaches nothing concerning enzymatic coupling reactions using Z-Asp as a starting material in water.

Attention should, however, be drawn to DE-A-3517361, which discloses, for an enzymatic coupling reaction, that the reactants Z-Asp and L-PM may indeed be present in virtually stoichiometric ratios, but—for adduct formation—(and instead of the minimum equivalent excess required of L-PM or D-PM according to the state of the art cited hereinabove) an at least equivalent amount of an organic amine compound is employed, in which at least one $C_6$ hydrocarbon radical is present. In practice, such a method is of little relevance for the preparation of APM because, on the one hand, the addition product formed has to be cleaved by acidification, liberating the amine, and, on the other hand, a further organic component "foreign to the process" is introduced which, in recirculation and filtrate streams of the process, is difficult to separate from the starting materials used for the APM synthesis.

There was therefore a need for simple and efficient, preferably stoichiometric, enzymatic coupling of Z-Asp and L-PM, which affords both high conversion and low consumption of starting materials and a limitation in recycling streams, and yields a readily filterable product without the need for the presence of at least equivalent amounts of D-PM (or an additional equivalent of L-PM) or the like, and without the necessity of adding organic solvents or amines in the coupling reaction.

SUMMARY AND OBJECTS OF THE INVENTION

The object of the invention is to provide a simple process with a high degree of conversion for enzymatic coupling of Z-Asp and L-PM, in which the drawbacks mentioned above are avoided, stoichiometric or virtually stoichiometric amounts of reactants can be employed, and a readily filterable product is obtained. Surprisingly, this object is achieved according to the invention by the coupling reaction being carried out with the aid of equimolar or virtually equimolar quantities of Z-Asp and L-PM under the influence of a neutral protease as an enzyme at an initial pH of from 4.5 to 6.0 and in the presence of from 3 to 25%, calculated as per cent by weight based on the total reaction mixture, of an alkali metal salt, alkaline earth metal salt or an ammonium salt. In connection with the reaction rate and to limit undesirable hydrolysis, the coupling reaction is preferably carried out at an initial pH of from 4.7 to 5.5.

It was also found, surprisingly, that when carrying out the process according to the invention, the coupling reaction can also be carried out very conveniently at relatively high concentrations of starting materials. Such high concentrations have been found to be impossible in the processes according to the state of the art, owing to the viscosity of the reaction system rising to excessive levels during the course of the reaction. Without commitment to any particular explanation, Applicant assumes that the advantageous results of the present invention may be ascribed to differences in solubility of Z-APM and of Z-APM.L-PM at different pH values and salt concentrations.

DETAILED DESCRIPTION OF THE INVENTION

In the process according to this invention an aqueous medium is used which contains an alkali metal salt, alkaline earth metal salt or ammonium salt in an amount of from 3 to 25%, calculated as per cent by weight based on the total reaction mixture, and an initial pH of from 4.5 to 6.0 to carry out an enzymatic coupling reaction with a neutral protease between Z-protected aspartic acid and L-phenylalanine methyl ester in stoichiometric or virtually stoichiometric ratios, with the formation of a precipitate.

The term aqueous medium, in the context of the present application, refers to any homogeneous, polar aqueous system, which may contain small amounts (up to approximately 30%) of an organic solvent such as, for example, methanol or acetonitrile.

All kinds of alkali metal salts, alkaline earth metal salts or ammonium salts can be used in the process according to the invention. Suitable salts are, for example, halides or sulphates of potassium, sodium, lithium, calcium, magnesium and ammonium, or mixtures thereof. The term ammonium here also refers to ammonium substituted with one or more $C_{1-3}$ alkyl groups; examples of such substituted ammonium salts are tri(m)ethylammonium chloride, di(m)ethylammonium chloride, etc. As far as the percentage by weight range is concerned, which according to the invention is in the range from 3 to 25 wt. %, the potential applications are partially determined by the solubility of the respective salts. Alkali metal and ammonium salts generally have the best solubility and are to be preferred. Particular preference is given to use of lithium chloride, sodium chloride, potassium chloride, sodium sulphate, potassium sulphate, ammonium chloride and/or ammonium sulphate.

The higher the salt content in the reaction system, the faster conversion proceeds, without the yields being affected significantly. At higher contents, however, the viscosity of the system will soon increase strongly and/or the solubility limit of one or more of the starting materials and/or of the salt itself will be exceeded, so that the precipitate obtained is unnecessarily contaminated with said salt, or so that the degree of conversion of the reaction is lower. Above 25%, the viscosity of the system makes it virtually impossible to carry out the reaction. The lower the salt content in the reaction system, the longer the total reaction time required will be, giving rise to increased hydrolysis of, in particular, L-PM. At contents below 3%, the presence of salt is deemed to have no significant effect on the reaction. At lower salt concentrations there also is an undesirable effect on the solubility of the coupling product. If the addition product (Z-APM.L-PM) should precipitate prematurely, this, incidentally, does not interfere in the reaction according to the invention since the shift in equilibrium will automatically result in conversion of all or part of this product into Z-APM precipitate during the course of the reaction under the specific conditions in question. Preferably, the salt content is from 10 to 18%, because in that range the most favourable conditions are found with respect to a) the viscosity of the system; b) the solubility of the starting materials and precipitate formation of the end product; and c) the reaction time. This will be clarified hereinafter in more detail during the discussion of the mechanical conditions to which the system is subject.

The enzymatic coupling as a rule takes place within a temperature range of from 10° to 60° C. The lower the temperature, the lower the rate at which both the coupling reaction and the side reactions, such as hydrolysis of L-PM and Z-APM, proceed. The higher the temperature, the faster deactivation of the enzyme will occur. Those skilled in the art can readily determine what temperature should be chosen for the enzyme used in order to achieve optimum results in terms of conversion to Z-APM and life of the enzyme.

The enzymatic coupling according to the invention is carried out using a neutral protease. The term neutral protease here refers to any known neutral proteolytic enzyme which can be used in the synthesis of Z-APM from Z-Asp and L-PM, as well as mutants thereof having a comparable or even increased activity. Examples are metallo-proteases such as thermolysin, produced by *Bacillus thermoproteolyticus*, and other proteases produced, inter alia, by various *Bacillus* species, such as *Bacillus stearothermophilus*, *Bacillus amyloliquefaciens*, *Bacillus cereus*, collagenase, etc. In general, these enzymes exhibit an optimum in protease activity at a pH of from approximately 6 to 8, but it has been found that, when they are used under the conditions according to the present invention, good results are also achieved at the initial pH of from 4.5 to 6.0, in particular from 4.7 to 5.5, without the need to employ excessive additional amounts of enzyme. It should be noted that the presence of small amounts of $Ca^{2+}$ ions in general has a beneficial effect on the stability and the action of the enzyme.

The values of the pH range (indicated as initial pH) within which the invention can be used with good results should be understood, in the context of the present application, as the value of the pH in the aqueous reaction system at the beginning of the enzymatic coupling; during the coupling reaction according to the invention as a rule first a small decrease of the pH is observed, whereafter an increase occurs as the reaction proceeds. During both the decrease and the increase said pH limits can be breached without an adverse effect on the results. It is preferable, however, for the pH during the coupling reaction, and in particular during the later phase thereof, to be held at a level below 6.2, preferably below 5.7.

At an initial pH below 4.5 the degree of conversion and the yields decrease due to lower enzyme activity. At an initial pH above 6.0, the degree of conversion and the yield also decrease, inter alia because of an increase in undesirable hydrolysis of the esters, as well as formation of Z-APM.L-PM, which under these conditions is no longer converted into Z-APM. Incidentally, it should be noted that these limits of the pH may also vary to a small extent, depending on the enzyme used. Thus, for example, when working with a mutant enzyme which is active at a lower pH, a further lowering of the lower limit of the pH range, for example to 3.5 to 4, will be achievable.

At the end of the reaction cycle, i.e. when attaining the ultimate degree of conversion, the activity of the enzyme has, as a rule, not changed or hardly changed, which permits reuse of the enzyme. Consequently, it is recommended—in particular when using dissolved enzymes—for the enzyme to be reemployed for the enzymatic coupling reaction after separation of the precipitate obtained. In so doing, where necessary the composition of the aqueous medium should be adjusted slightly until the correct starting conditions have again been obtained. The enzymatic coupling reaction can thus be repeated several times with the same amount of enzyme; if the initial activity falls off slightly, fresh enzyme is added, if required, so that the desired degree of conversion is attained within a time acceptable for this purpose.

Where mention is made in this application of Z-, this should also be understood to refer to any protective group related, in terms of apolar character, to Z-, such as, for example, benzyloxycarbonyl compounds substituted in the benzyl ring by one or more alkyl, alkoxy, acyl or halogen groups. Where reference is made in this application to L-phenylalanine methyl ester (L-PM), this should also be understood to refer to the acid salts derived therefrom, such as, for example, the hydrochloride (L-PM.HCl). Where reference is made in this application to benzyloxycarbonyl aspartic acid (Z-Asp), this should also be understood as referring to the salts derived therefrom, such as, for example, the disodium salt (Z-Asp.diNa). Obviously, when using an acid salt instead of L-PM and/or a salt instead of Z-Asp, it will be necessary, to a limited extent, to adjust the amounts of chemicals to be employed to achieve the pH to be set.

The terms stoichiometric or virtually stoichiometric ratios are understood, in the present application, to refer to a Z-Asp:L-PM molar ratio in the range of from 1:0.7 to 0.7:1. Preferably, a molar ratio of from 1:0.8 to 1:1 is used. A slight excess of Z-Asp leads to the best results in terms of degree of conversion and yield. In the 1:1 situation, any required recycling of one or both of the unreacted starting materials is minimized.

It is found that in the process according to the invention the precipitate differs—both in terms of chemical composition and in terms of crystal properties and filterability—from the Z-APM.(D/L)-PM addition product which is obtained in the process according to the state of the art. Notably, the crystals obtained are larger, and the filtration rate is therefore likewise higher, with the result that purification of the product is simpler because fewer impurities are trapped or remain behind in adherent moisture.

Applicant has found that, as far as carrying out the reaction is concerned, many forms are possible, both in terms of apparatus and in terms of the nature of the means which may be used to set or keep the system in motion, if required. The coupling reaction can be carried out in all kinds of vessels and columns, made from materials such as glass, stainless steel, etc. which do not interfere with the reaction in a detrimental manner. Columns are especially suitable when immobilized enzymes such as supported enzymes are used. The dimensions of the equipment may vary within wide limits. The reaction can therefore be carried out on any scale desired, from a test tube or beaker to, for example, a scale of 10 m$^3$.

It is also possible to opt for either batchwise or partially continuous reaction. If the process of the present invention is carried out (semi-)continuously, continuous separation of the precipitate will preferably be initiated only from the instant when at least approximately 60% of the conversion of the initial reaction mixture has been achieved, whereafter further dosing of the starting materials in virtually stoichiometric ratios can be effected to the extent in which the precipitate is separated.

The conversion according to the invention proceeds very well without any mechanical influence being exerted on the reaction system, in which case so-called static conditions are present. The chosen reactor then does not have to be equipped with a stirrer or means which keep the reaction medium in motion in some other way. Excellent results are also achieved if the reaction system is kept in more or less violent motion, either continuously or intermittently, for example by mechanical stirring or by keeping the reaction vessel in motion by shaking. The terms stirring and shaking in this context comprise all embodiments which may be considered by those skilled in the art. Thus, for stirring purposes in principle any type of stirrer can be used; there are advantages, however, in using variable-speed stirrers, because the stirring speed can then be set to an optimum and may even be adjusted to changes in viscosity and the like. The effects of the stirring speed, incidentally, are only small. Circulating the contents of the reaction vessel by means of an external pump should be regarded as a form of stirring. The pumping rate and the dimensions of the reaction vessel then determine the degree of mixing in the system. It will be obvious that variants in which shaking is used are more suitable when the reaction is carried out on a relatively small scale, up to approximately 1000 l. The experiments carried out by Applicant have shown that very high degrees of conversion are achieved when using the "shaking method". An embodiment that is also found to be very suitable is one in which the first part of the reaction is carried out under static conditions, until approximately from 20 to 60%, preferably from 30 to 50%, of the conversion has been achieved, and the reaction is then continued under stirred conditions until the desired degree of conversion has been achieved. All possible combinations of these "mechanical" treatments can likewise be used within the scope of the invention.

The amount of enzyme used in the coupling reaction is not critical, but as a rule such an amount of enzyme will be used that the duration of the reaction until a high degree of conversion (>60, preferably >80%) is reached, will not be more than 150 hours. As a rule, amounts of enzyme (which is here understood to be the protein having the enzyme activity in question, the so-called active protein) of from 0.08 to 1.5%, preferably from 0.15 to 0.75%, expressed as per cent by weight based on the total reaction mixture, are suitable. The percentages mentioned here as a rule correspond to from approximately 0.5 to 10%, or preferably from 1 to 5%, if the amount of enzyme is given as the total amount of (dry) enzyme preparation employed, i.e. active protein and other proteins as well as other adjuvants such as salts. The enzymes will often be employed as an enzyme preparation and are also commercially available as such. Usually, the amount of active protein in such a preparation is approximately 15% of the weight of the preparation.

In the process according to the invention the enzyme can be used in any form suitable for this purpose, i.e. both in dissolved and in immobilized form. Preferably, use is made of dissolved enzyme (obtained by dissolving an enzyme preparation in the reaction medium), as this has advantages in the separation of the precipitate obtained and further processing thereof, as well as in the reuse of the biocatalyst itself. As stated earlier, it is also possible to use mutants of the enzymes in question. The percentages specified hereinabove for the amount of enzyme can vary, depending on the activity of the enzyme to be used, and certainly when mutants are used.

The concentrations of the starting materials Z-Asp and L-PM may likewise vary within wide limits and are determined, inter alia, by the solubility of these materials in the initial reaction mixture. However, the presence of small amounts of undissolved starting materials does not interfere with the course of the reaction, since these amounts will pass into solution during the reaction. In state-of-the-art processes it is impossible, as a result of product inhibition and in connection with the viscosity rising to excessive levels during the reaction, to carry out the reaction at molar concentrations of the starting materials above approximately from 200 to 700 mM; the present invention makes it possible to achieve good conversions even at higher molar concentrations of the starting materials and therefore also of the coupling product, up to the order of magnitude of approximately 1200 mM. This signifies an additional advantage of the process according to the invention, because it is thus possible to achieve an improved output per reactor volume.

The invention will now be explained in more detail with reference to the following examples and the comparative example, without however being limited thereto. Beforehand, it should be noted that the compositions of the reaction mixture, given in the examples (molar concentrations and per cent by weight in the initial situation) are calculated on the basis of the accurately determined amounts employed and the weight and volume of the prepared reaction mixture. The degrees of conversion (and likewise the results as regards L-PM hydrolysis which has occurred at the end of the reaction time) were determined by means of so-called reversed-phase high performance liquid chromatography (reversed-phase HPLC), using UV-spectrophotometric detection at 257 nM, use being made of a column packed with Nucleosil C18 and a multigradient eluent system (water/acetonitrile/triethylammonium phosphate) at pH 3.0. The samples taken from the reaction mixture were in each case immediately taken up in methanol in order to stop the enzymatic reaction, and they were stored at low temperature prior to being analyzed (via auto-injection into the continuous stream of the eluent). The enzyme concentrations and initial enzyme activities specified in the following examples are in each case calculated on the basis of the amount of enzyme preparation employed. The specified values for L-PM hydrolysis are determined at the end of the reaction and are expressed as average hydrolysis per hour in per cents based on the amount of L-PM present at the outset.

EXAMPLE I

An amount of L-PM.HCl (4.01 g; 18.6 mmol) was admixed at room temperature, in a 100 ml beaker and with stirring, with a solution of Z-Asp.diNa (7.28 g; 23.4 mmol) in water (20.57 g). Successively, the solution obtained was admixed, likewise with stirring, with 2.59 g NaCl and 0.17 g $CaCl_2.2H_2O$, and the pH was then set, by adding 3N HCl, to 5.0. The clear solution remaining was then admixed with 2.98 g of thermolysin (powder, from Daiwa; containing approximately 15% of thermolysin protein and 70% NaCl). Thus a reaction mixture was obtained having the following composition:
Total weight: 39.7 g
Total volume: 33.1 ml
$[Z-Asp]_0$: 707 mM (26% excess based on L-PM)
$[L-PM]_0$: 562 mM
[NaCl]: 14.5%
[enzyme]: 7.5% (preparation)
pH: 5.0
Portions of, in each case, approximately 2.0 ml of this reaction mixture were immediately transferred to 15 test tubes which were then simultaneously placed in a water bath of 40° C., suspended in holders linked to a shaking machine (Gyrotory Water Bath Shaker, Model G76D from New Brunswick Scientific Co. Inc.). The shaking machine was set to a speed of 200 revolutions per minute. After certain intervals one test tube at a time was taken from the water bath in order to determine the progress of the reaction. To this end, the tube, after the addition of approximately 15 ml of methanol so as to stop the reaction, was cooled to approximately 5° C., after which the composition of the contents was analyzed with the aid of reversed-phase HPLC. An initial enzyme activity of 32 $nmol.min^{-1}mg^{-1}$ of enzyme preparation was found. In addition, it was established that the first precipitate was present after approximately 30 minutes and that an ultimate degree of conversion (calculated on the basis of L-PM) of 87% was achieved after a reaction time of 2.5 hours. If the reaction lasted longer, no further increase in the degree of conversion occurred. After a reaction time of 2.5 hours, there was no detectable formation of L-Phe. Under these conditions, therefore, no hydrolysis of L-PM takes place.

EXAMPLE II

A suspension of L-PM.HCl (3.34 g; 15.5 mmol) and Z-Asp (4.96 g; 18.6 mmol) in water (14.9 g) was admixed, at room temperature, in a beaker and with stirring, with a quantity of 22% NaOH by weight (6.72 g; 37.0 mmol NaOH), so that a clear solution was formed having a pH=5.0. Successively, likewise with stirring, this solution was admixed with 3.26 g of NaCl, 0.12 g of $CaCl_2.2H_2O$ and 1.40 g of thermolysin (powder, from Amano; containing approximately 15% of thermolysin protein and 34% of NaCl). Thus a reaction mixture was obtained having the following composition:
Total weight: 34.7 g
Total volume: 29.3 ml
$[Z-Asp]_0$: 634 mM (20% excess based on L-PM)
$[L-PM]_0$: 529 mM
[NaCl]: 13.5%
[enzyme]: 4.0%
pH: 5.0
The reaction mixture was immediately distributed between test tubes and treated further as described in Example I. An initial enzyme activity of 27 $nmol.min^{-1}mg^{-1}$ of enzyme preparation was found. It was also found that the first precipitate could be observed after approximately 120 minutes, and that an ultimate degree of conversion (based on L-PM) of 80% had been achieved after a reaction time of 9 hours. As the reaction continued, no further increase in the degree of conversion occurred. After a reaction time of 9 hours, a small amount of L-Phe (0.21 mmol) had been produced, corresponding to a hydrolysis of L-PM of 0.16% per hour.

EXAMPLE III

The procedure of Example II was repeated, except that now the amounts of initial materials mentioned below in parentheses were employed:
L-PM.HCl (4.70 g; 21.8 mmol); Z-Asp (5.28 g; 19.8 mmol); water (13.68 g); 22% NaOH (6.36 g; 35.0 mmol NaOH); NaCl (2.95 g); $CaCl_2.2H_2O$ (0.13 g); thermolysin (powder, from Amano, 1.50 g; as in Example II).
This resulted in the following composition of the initial reaction mixture:
Total weight: 34.6 g
Total volume: 29.0 ml
$[Z-Asp]_0$: 683 mM
$[L-PM]_0$: 752 mM (10% excess based on Z-Asp)
[NaCl]: 13.7%
[enzyme]: 4.3%
pH: 5.0
The reaction mixture was immediately distributed between test tubes and treated further as described in Example I. An initial enzyme activity of 32 $nmol.min^{-1}mg^{-1}$ of enzyme preparation was found. It was also observed that the first precipitate had formed after approximately 60 minutes. A degree of conversion (based on L-PM) of 57% had been achieved after a reaction time of 13.5 hours, and as the reaction continued, some further increase in the degree of conversion occurred. After a reaction time of 13.5 hours, a small amount of L-Phe (0.32 mmol) was observed, corresponding to a hydrolysis of L-PM of approximately 0.1% per hour.

EXAMPLE IVa

The procedure of Example II was repeated, except that now the amounts of initial materials mentioned below in parentheses were employed:
L-PM.HCl (4.31 g; 20.0 mmol); Z-Asp (5.87 g; 22.0 mmol); water (14.53 g); 22% NaOH (6.89 g; 37.9 mmol NaOH); NaCl (3.20 g); $CaCl_2.2H_2O$ (0.12 g); thermolysin (Amano, 1.42 g; as in Example II). This resulted in the following composition of the initial reaction mixture:
Total weight: 36.3 g
Total volume: 30.8 ml
$[Z-Asp]_0$: 714 mM (10% excess based on L-PM)
$[L-PM]_0$: 649 mM
[NaCl]: 13.4%
[enzyme]: 3.9%
pH: 5.0
The reaction mixture was immediately distributed between test tubes and treated further as described in Example I. An initial enzyme activity of 27.9 $nmol.min^{-1}mg^{-1}$ of enzyme preparation was found. It was also found that a degree of conversion (based on L-PM) of 83% had been achieved after a reaction time of 15 hours, and that no further increase in the degree of conversion occurred as the reaction continued.

After a reaction time of 15 hours only a very small amount of L-Phe was observed, corresponding to a hydrolysis of 0.2% per hour.

EXAMPLE IVb

The procedure of Example IVa was repeated, except that different amounts of water, 22% NaOH and NaCl were employed, viz.: water (13.58 g); 22% NaOH (7.30 g; 40.1 mmol); NaCl (4.60 g). This resulted in the following composition of the initial reaction mixture:
Total weight: 37.2 g
Total volume: 31.2 ml
$[Z-Asp]_0$: 706 mM (10% excess based on L-PM)
$[L-PM]_0$: 641 mM
[NaCl]: 17.2%
[enzyme]: 3.8%
pH: 5.0
The reaction mixture was immediately distributed between test tubes and treated further as described in Example I. An initial enzyme activity of 42.0 nmol.min$^{-1}$mg$^{-1}$ of enzyme preparation was found. It was also found that a degree of conversion (based on L-PM) of 77% had been achieved after a reaction time of approximately 4 hours, and that no further increase in the degree of conversion occurred as the reaction continued. After a reaction time of 4 hours, a small amount of L-Phe (0.23 mmol) was observed, i.e. a hydrolysis of 0.16% per hour.

EXAMPLE IVc

The procedure of Example IVa was again repeated, except that again different amounts of water, 22% NaOH and NaCl were employed, viz: water (15.78 g); 22% NaOH (6.82 g; 37.5 mmol); NaCl (2.00 g). This resulted in the following composition of the initial reaction mixture:
Total weight: 36.3g
Total volume: 30.8 ml
$[Z-Asp]_0$: 714 mM (10% excess based on L-PM)
$[L-PM]_0$: 649 mM
[NaCl]: 10.0%
[enzyme]: 3.9%
pH: 5.0
The reaction mixture was immediately distributed between test tubes and treated further as described in Example I. An initial enzyme activity of 18.0 nmol.min$^{-1}$mg$^{-1}$ of enzyme preparation was found. It was also found that a degree of conversion (based on L-PM) of 84% had been achieved after a reaction time of approximately 16 hours, and that no further increase in the degree of conversion occurred as the reaction continued. After a reaction time of 16 hours, an amount of L-Phe (1.1 mmol) was observed, corresponding to a hydrolysis of 0.3% per hour.

EXAMPLE V

The procedure of Example II was repeated, except that now the amounts of initial materials mentioned below in parentheses were employed, and that, in order to determine effects of the degree of movement, tests were also carried out at different shaking speeds and under static conditions:
L-PM.HCl (12.93 g; 60.0 mmol); Z-Asp (18.33 g; 68.6 mmol); water (43.86 g); 22% NaOH (19.99 g; 109.9 mmol NaOH); NaCl (9.75 g); CaCl$_2$.2H$_2$O (0.42 g); thermolysin (powder, from Amano, 4.26 g; as in Example II). This resulted in the following composition of the initial reaction mixture:
Total weight: 109.5 g
Total volume: 91.2 ml
$[Z-Asp]_0$: 752 mM (14% excess based on L-PM)
$[L-PM]_0$: 658 mM
[NaCl]: 13.4%
[enzyme]: 3.9%
pH: 5.0
Of the reaction mixture obtained, 15 ml was immediately transferred to a glass reaction vessel having a diameter of 3.3 cm which was placed in a water bath of 40° C., suspended in a holder linked to a shaking machine. The shaking machine was set to a speed of 150 revolutions per minute.

At the same time, a second 15 ml portion of the same reaction mixture was treated in a similar manner in another shaking machine, set to a speed of 250 revolutions per minute. In addition, a third portion, 10 ml, was stored under static conditions at 40° C.

After certain intervals samples were taken from the vessels to determine the progress of the reaction, (the first samples—which still contained no or only small amounts of precipitate—with the aid of a pipette; later samples, when the viscosity of the reaction mixture had increased as a result of precipitation, with the aid of a spatula). To this end the samples taken were diluted with approximately 15 ml of methanol, cooled to approximately 5° C. and analyzed for their composition with the aid of reversed-phase HPLC. Initial enzyme activities of 37.8, 30.0 and 21.0 nmol.min$^{-1}$mg$^{-1}$ of enzyme preparation, respectively, were found (at 150 rpm, 250 rpm and under static conditions, respectively). It was also found that in the three situations, after a reaction time of as little as 8 hours (150 rpm) and 12 hours, respectively, a degree of conversion (based on L-PM) of approximately 89% was achieved, and that, as the reaction continued, there was no further increase in the degree of conversion. In these three situations, the L-PM hydrolysis amounted to approximately 0.2% per hour. A quantity of the precipitate present after 4 hours in the situation where shaking had been applied was in addition analyzed for its chemical composition and was found to consist of Z-APM to at least 98%.

EXAMPLE VI

A further 50 ml portion of the initial reaction mixture as prepared in Example V was transferred to a thermostatted glass reaction vessel having a diameter of approximately 5 cm which was kept at 40° C. and was provided with a variable-speed stirrer with blades placed just above the bottom and just below the liquid level. The speed of the stirrer was set to 60 revolutions per minute. After certain intervals samples were taken, as in Example V, with a pipette and with a spatula, respectively, and analyzed. An initial enzyme activity of 20.1 nmol.min$^{-1}$mg$^{-1}$ of enzyme preparation was found. It was also observed that, after a reaction time of 25 hours, a degree of conversion (based on L-PM) of 67% had been reached, and that the degree of conversion increased still further as the reaction continued. After a reaction time of 25 hours, a small amount of L-Phe (0.55 mmol) was observed, i.e. the hydrolysis amounted to 0.07% per hour.

The composition of the precipitate as obtained after 4 and 20 hours, respectively, was analyzed, and was found to be different at the two times: after 4 hours, 98% was present as Z-APM.L-PM and 2% as Z-APM, but after 20 hours these percentages had changed to 67% and 33%, respectively.

EXAMPLE VII

In analogy to the starting solution of Examples V and VI, starting solutions were also prepared in which the salt content of 13.4% by weight was achieved using—mainly—KCl or $Na_2SO_4$, the compositions otherwise being identical. In mixture A, 12.1% KCl and 1.3% NaCl were present; in mixture B, 8.9% $Na_2SO_4$ and 4.5% NaCl. When the coupling reaction was carried out, results comparable to the results of Examples V and VI were found.

EXAMPLE VIII

In the same manner as described in Example V, a new reaction mixture was prepared. Of this, 50 ml were immediately transferred to the thermostatted glass reaction vessel of Example VI, which was kept at 40° C. Now, however, the stirrer was only started after 5 hours' reaction under static conditions and was then set to 60 revolutions per minute. After certain intervals, samples were taken as in Example V and analyzed. An initial enzyme activity of 20.6 $nmol.min^{-1}mg^{-1}$ of enzyme preparation was found. The degree of conversion after 5 hours was 43%. It was also observed that, after a reaction time of 20 hours, a degree of conversion (based on L-PM) of 86% had been reached, and that the degree of conversion increased even further as the reaction continued. After a reaction time of 25 hours, a small amount of L-Phe (1.1 mmol) was observed, corresponding to a degree of hydrolysis of approximately 0.17% per hour.

EXAMPLE IX

A reaction mixture (total weight: 339.96 g; total volume: 275.6 ml) was prepared having the following composition:
$[Z-Asp]_0$: 745 mM (14% excess based on L-PM)
$[L-PM]_0$: 653 mM
[ NaCl]: 13.0%
[enzyme]: 3.8% (preparation; thermolysin from Amano)
pH: 5.3
This mixture was divided into three portions (A, B, C) of 90 ml, which portions were employed as described in Example VI. The pH of portion A was not influenced further during the coupling reaction; the pH of portion B was held at approximately 5.3 by dropwise metering-in of NaOH solution (if the pH decreased) and HCl solution (if the pH increased); in the case of portion C, care was taken to keep the pH at approximately 5.3 by dropwise metering-in of HCl solution (when the pH rose above 5.3).

Both in the coupling reaction with portion A and in the reaction with portion B, crystals had formed already after 30 minutes, which took approximately 1 hour in the case of portion C. In portion A (with an initial enzyme activity of 33.0 $nmol.min^{-1}mg^{-1}$ of enzyme preparation) a degree of conversion of approximately 70% had been attained after 24 hours, which did not increase as the reaction continued; the final pH was 6.16 and the PM hydrolysis was approximately 0.1% per hour. In portions B and C (having the same initial enzyme activity) a degree of conversion of 95 to 96% was attained after 60 and 45 hours, respectively, and a PM hydrolysis of approximately 0.07% per hour was observed.

COMPARATIVE EXAMPLE A

The procedure of Example II was repeated, except that now the amounts of initial materials mentioned below in parentheses were employed and a pH of 6.0 was set: L-PM.HCl (4.04 g; 18.8 mmol); Z-Asp (5.34 g; 20.0 mmol); water (44.35 g); 22% NaOH (7.56 g; 41.6 mmol NaOH); NaCl (8.08 g); CaCl $2.2H_2O$ (0.12 g); thermolysin (powder, from Amano, 1.42 g; as in Example II). This resulted in the following composition of the clear solution of the initial reaction mixture:

Total weight: 70.1 g
Total volume: 61.7 ml
$[Z-Asp]_0$: 324 mM (6% excess based on L-PM)
$[L-PM]_0$: 305 mM
[NaCl]: 13.4%
[enzyme]: 1.0%
pH: 6.0
This reaction mixture was distributed between test tubes and treated further as described in Example I. An initial enzyme activity of 61 $nmol.min^{-1}mg^{-1}$ of enzyme preparation was found. It was also found that an ultimate degree of conversion (based on L-PM) of 46% had been achieved after a reaction time of 3 hours, and that no increase in the degree of conversion occurred as the reaction continued. After a reaction time of 3 hours it was also found, incidentally, that 0.65 mmol of L-Phe had formed, produced by hydrolysis of L-PM (i.e. approximately 1.15% per hour, based on the initial 18 mmol).

We claim:

1. Process for the preparation of N-benzyloxycarbonyl-α-L-aspartyl-L-phenylalanine methyl ester by high-conversion enzymatic coupling of N-benzyloxycarbonyl-L-aspartic acid and L-phenylalanine methyl ester in an aqueous medium with formation of a precipitate, characterized in that the coupling reaction is carried out using equimolar or virtually equimolar quantities of N-benzyloxycarbonyl-L-aspartic acid and L-phenylalanine methyl ester under the influence of a neutral protease as enzyme at an initial pH of from 4.5 to 6.0 and in the presence of from 3 to 25%, calculated as per cent by weight based on the total reaction mixture, of an alkali metal salt, alkaline earth metal salt or ammonium salt.

2. Process according to claim 1, characterized in that the initial pH is in the range of from 4.7 to 5.5.

3. Process according to claim 2 characterized in that the alkali metal salt, alkaline earth metal salt or ammonium salt is present in an amount of from 10 to 18%.

4. Process according to claim 1, characterized in that the alkali metal salt or ammonium salt used is lithium chloride, sodium chloride, potassium chloride, sodium sulphate, potassium sulphate, ammonium chloride and/or ammonium sulphate.

5. Process according to claim 1, characterized in that the coupling is carried out in the presence of from 0.08 to 1.5 percent by weight of enzyme (active protein) based on the total reaction mixture.

6. Process according to claim 1, characterized in that use is made of a dissolved enzyme.

7. Process according to claim 1, characterized in that amounts of N-benzyloxycarbonyl-L-aspartic acid and L-phenylalanine methyl ester are used in a molar ratio in the range of from 1:0.7 to 0.7:1.

8. Process according to claim 7, characterized in that the molar ratio of N-benzyloxycarbonyl-L-aspartic acid and L-phenylalanine methyl ester is in the range of from 1:0.8 to 1:1.

9. Process according to claim 1, characterized in that the pH of the aqueous reaction system of the coupling reaction is maintained at a level below 6.2.

10. Process according to claim 1, characterized in that the coupling is carried out under such conditions that the reaction mixture is kept in motion at least during parts of the coupling process.

11. Process according to claim 1, characterized in that the reaction mixture is kept in motion by shaking at least during parts of the coupling process.

12. Process according to claim 1, characterized in that the coupling reaction is carried out semi-continuously, with continuous removal of the precipitate taking place from the moment that at least 60% conversion of the initial reaction mixture has been achieved, and with further addition of the starting materials from that same moment in virtually stoichiometric proportion.

13. Process according to claim 1, characterized in that the first part of the coupling process, until approximately 20–60% of the conversion has been attained, is carried out under static conditions and then the reaction mixture is kept in motion at least during parts of the subsequent coupling process.

14. Process according to claim 5, characterized in that the coupling is carried out in the presence of from 0.15 to 0.75 percent by weight of enzyme (active protein), based on the total reaction mixture.

15. Process according to claim 1, characterized in that the pH of the aqueous reaction system of the coupling reaction is maintained at a level below 5.7.

16. Process according to claim 1, characterized in that said coupling reaction is carried out in the presence of from 10 to 18 percent, calculated as percent by weight based on the total reaction mixture, of an alkali metal salt, alkaline earth metal salt or ammonium salt.

17. Process according to claim 1, characterized in that the initial pH is in the range of 4.7 to 5.5, the coupling is carried out in the presence of from 0.15 to 0.75 percent by weight of enzyme (active protein) based on the total reaction mixture, the mole ratio of N-benzyloxycarbonyl-L-aspartic acid and L-phenyl alanine methyl ester is in the range of 1:0.8 to 1:1.

18. Process according to claim 17, characterized in that and alkali metal salt or an ammonium salt is used, and said salt is at least one selected from the group consisting of lithium chloride, sodium chloride, potassium chloride, sodium sulphate, potassium sulphate, ammonium chloride and ammonium sulphate.

19. Process according to claim 6, characterized in that the initial pH is in the range of 4.7 to 5.5, the coupling is carried out in the presence of from 0.15 to 0.75 percent by weight of enzyme (active protein) based on the total reaction mixture, the mole ratio of N-benzyloxycarbonyl-L-aspartic acid and L-phenyl alanine methyl ester is in the range of 1:0.8 to 1:1.

20. Process according to claim 19, characterized in that the initial pH is in the range of 4.7 to 5.5, the coupling is carried out in the presence of from 0.15 to 0.75 percent by weight of enzyme (active protein) based on the total reaction mixture, the mole ratio of N-benzyloxycarbonyl-L-aspartic acid and L-phenyl alanine methyl ester is in the range of 1:0.8 to 1:1 .

* * * * *